United States Patent [19]

Witte et al.

[11] Patent Number: 4,981,873
[45] Date of Patent: Jan. 1, 1991

[54] SUBSTITUTED SULPHONAMIDES, PHARMACEUTICALS THEREOF AND METHODS OF USING THEM

[75] Inventors: Ernst-Christian Witte, Mannheim; Karlheinz Stegmeier, Heppenheim; Liesel Doerge, Lampertheim, all of Fed. Rep. of Germany; Robert A. Slater, Letchworth, England

[73] Assignee: Boehringer Mannheim GmbH, Mannheim, Fed. Rep. of Germany

[21] Appl. No.: 370,455

[22] Filed: Jun. 23, 1989

[30] Foreign Application Priority Data

Jun. 25, 1988 [DE] Fed. Rep. of Germany ....... 3821540

[51] Int. Cl.$^5$ .................... A61K 31/19; C07D 257/04; C07C 317/14; C07C 317/02
[52] U.S. Cl. .................... 514/562; 514/155; 514/158; 514/381; 514/538; 514/539; 514/549; 514/550; 548/252; 560/16; 562/430
[58] Field of Search .................... 562/430; 560/16; 514/155, 158, 381, 538, 539, 549, 550, 562; 548/252

[56] References Cited

U.S. PATENT DOCUMENTS 4,849,563 7/1989 Sartorelli et al. ............... 562/430 X Primary Examiner—Werren B. Lone
Assistant Examiner—Vera C. Clarke
Attorney, Agent, or Firm—Felfe & Lynch

[57] ABSTRACT

The present invention concerns compounds of the formula:

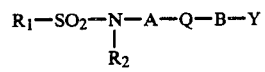

where $R_1$ is an alkyl or alkenyl radical containing up to 6 carbon atoms, a cycloalkyl radical containing 3 to 7 carbon atoms, an aralkyl, aralkenyl or aryl radical in which the aryl radical or moiety can be substituted one or more times by halogen, $C_1$-$C_6$-alkyl, $C_1$-$C_6$-alkoxy, hydroxyl, trifluoromethyl, cyano, nitro, amino, $C_1$-$C_6$-alkylamino, $C_2$-$C_{12}$-dialkylamino, $C_1$-$C_6$-acylamino, $C_1$-$C_{16}$-acyl, $C_1$-$C_6$-alkylsulphenyl, -sulphinyl or -sulphonyl or by azido, $R_2$ is hydrogen atom or a $C_1$-$C_6$-alkyl, aralkyl, aralkenyl or acyl radical, A and B are saturated or unsaturated alkylene chains containing up to 10 carbon atoms which can be substituted one or more times by $C_1$-$C_3$-alkyl radicals, the sum of carbon atoms in chains A and B being at least 4 and at most 11, Q is an oxygen or sulphur atom, a sulphonyl or sulphinyl group or an amino group —N($R_2$)—, $R_2$ having the same meaning as above, and Y is a free carboxylic acid group or a carboxylic acid ester, carboxylic acid amide, hydroxymethyl or tetrazolyl radical; the pharmacologically acceptable salts thereof and the optically active and E-Z isomers thereof, as well as mixtures thereof.

These compounds are useful as they have an antagonistic action towards thromboxane $A_2$ as well as against prostaglandin endoperoxide. They inhibit the aggregation of blood platelets and prevent the constriction of the smooth musculature as well as bronchoconstriction.

19 Claims, No Drawings

SUBSTITUTED SULPHONAMIDES, PHARMACEUTICALS THEREOF AND METHODS OF USING THEM

The present invention is concerned with new substituted sulphonamides, processes for the preparation thereof and pharmaceutical compositions containing them.

The new substituted sulphonamides according to the present invention are compounds of the general formula:

$$R^1-SO_2-N(R^2)-A-Q-B-Y \quad (I)$$

wherein $R^1$ is an alkyl or alkenyl radical containing up to 6 carbon atoms, a cycloalkyl radical containing 3 to 7 carbon atoms, an aralkyl, aralkenyl or aryl radical in which the aryl radical or moiety can be substituted one or more times by halogen, $C_1$-$C_6$-alkyl, $C_1$-$C_6$-alkoxy, hydroxyl, trifluoromethyl, cyano, nitro, amino, $C_1$-$C_6$-alkylamino, $C_1$-$C_{12}$-dialkylamino, $C_1$-$C_6$-acylamino, $C_1$-$C_{16}$-acyl, $C_1$-$C_6$-alkylsulphenyl, -sulphinyl or sulphonyl or by azido, $R^2$ is a hydrogen atom or a $C_1$-$C_6$-alkyl, an aralkyl, aralkenyl or acyl radical, A and B are saturated or unsaturated alkylene chains containing up to 10 carbon atoms which can be substituted one or more times by $C_1$-$C_3$-alkyl radicals, the sum of the carbon atoms in A and B being at least 4 and at most 11, Q is an oxygen or sulphur atom, a sulphonyl or sulphinyl group or an amino group $-N(R_2)-$, in which $R_2$ has the same meaning as above and Y is a free carboxylic acid group, a carboxylic acid ester group, a carboxylic acid amide group or a hydroxymethyl or tetrazolyl radical.

The new compounds of general formula (I) possess valuable pharmacological properties. In particular, they have an excellent antagonistic action towards thromboxane $A_2$, as well as against prostaglandin endoperoxide. They inhibit the aggregation of blood platelets and prevent the constriction of the smooth musculature, as well as bronchoconstriction. Furthermore, they are valuable agents for the treatment of pathological changes of renal function.

These properties make them valuable agents for the treatment of, for example, cardiovascular diseases and of asthma and for the prophylaxis of the shocked lung. Furthermore, they can be used in the case of organ transplants and in the case of renal dialysis and can be used for the prevention of recidivation in the case of gastric ulcers. Of special importance is the possibility of favourably influencing or preventing thrombotic processes. They can be used for the treatment of peripheral arterial occlusive diseases and can be used, for example, against cerebral and ischaemic states.

A and B are, in each case, acyclic, saturated or unsaturated hydrocarbon radicals containing up to 10 linear carbon atoms, of which one or more can be substituted at any desired position by one or two $C_1$-$C_3$-alkyl radicals which together can also form an alkylene chain $-(CH_2)_m-$, in which m is a whole number of from 2 to 5 and the sum of the chain carbon atoms of the chains A and B is at least 4 and at most 11.

Preferred hydrocarbon radicals A include the following: $-(CH_2)_n-$ in which n is a whole number of from 1 to 6, as well as $-(CH_2)_m-CH=CH-(CH_2)_n-$, in which m is 1 or 2 and n is 2, 3, 4 or 5.

Preferred hydrocarbon radicals B include the following: $-(CH_2)_p-$, in which p is a whole number of from 1 to 7, $-(CH_2)_q-C(CH_3)_2-$, in which q is 0 or a whole number of from 1 to 6, and $-(CH_2)_r-C(CH_3)_2-CH_2-$, in which r is 0 or a whole number of from 1 to 5.

Preferred substituents in the A and B chains are methyl and ethyl radicals and especially methyl radicals. If the two substituents of the A and B chains together signify an alkylene radical $-(CH_2)_m-$, then m is preferably 5 and it forms the basis of a six-membered ring when the substituents are on the same carbon atom.

Alkyl or alkenyl radicals $R_1$ are preferably methyl, ethyl, propyl and propenyl radicals and cycloalkyl radicals $R_1$ are preferably cyclopentyl, cyclohexyl and cycloheptyl radicals.

An aralkyl radical $R_1$ is preferably a benzyl or phenethyl radical, an aralkenyl radical $R_1$ is preferably a cinnamyl radical and an aryl radical $R^1$ is preferably a phenyl or naphthyl radical and the phenyl moieties in question can be substituted one or more times by halogen, methyl, methoxy, trifluoromethyl, cyano, nitro, amino, hydroxyl, methylamino, diethylamino, acetamino, acetyl, octanoyl, hexadecanoyl, methylsulphenyl, methylsulphinyl, methylsulphonyl or azide. Preferred radicals $R_1$ include 4-chlorophenyl, 4-bromophenyl, 4-fluorophenyl, 3-trifluoromethylphenyl, 4-methylphenyl, 4-cyanophenyl, 4-methoxyphenyl and 3-methylphenyl radicals and especially 4-chlorophenyl, 4-methoxyphenyl and 3-trifluoromethylphenyl radicals.

$R_2$ is normally a hydrogen atom but can also be a methyl, benzyl, 4-chlorobenzyl, cinnamyl, 4-chlorocinnamyl, benzoyl or acetyl radical.

The halogen atom can be a fluorine, chlorine or bromine atom.

The present invention includes all optical isomers, isomeric mixtures and racemates which result due to branching of the A and/or B chains. Furthermore, the present invention includes, when the chain A and/or B has an alkene character, all isomers which are thereby possible, i.e. the (Z) and the (E) forms and mixtures of the two.

When Q is an oxygen or sulphur atom or an $-NR^2-$ group, the compounds of general formula (I) are prepared by (a) reacting a compound of the general formula:

$$Z-O-A-X \quad (II),$$

in which A has the above-given meaning, Z is a protective group for the hydroxyl function and X is here and in all other cases a reactive residue, for example a halogen atom or a sulphonic acid ester radical, such as a mesylate or tosylate radical, in known manner with a compound of the general formula:

$$H-Q-B-Y \quad (III)$$

in which Q is an oxygen or sulphur atom or an $-NR^2-$ group and B and Y have the above-given meanings.

The protective group Z is subsequently split off to give a compound of the general formula:

$$HO-A-Q-B-Y \quad (IV)$$

in which A, B, Q and Y have the above-given meanings, the hydroxyl group of which is converted into an X group to give a compound of the general formula:

X—A—Q—B—Y  (V)

in which A, B, Q, X and Y have the above-given meanings, which is then reacted with a sulphonamide of the general formula:

$R^1$—$SO_2$—NH—$R^2$  (VI)

in which $R^1$ and $R^2$ have the above-given meanings.

(b) On the other hand, the compounds of general formula (I) can be prepared by reacting a compound of the general formula:

Z—O—A—Q—H  (VII)

in which A and Z have the above-given meanings and Q is an oxygen or sulphur atom or an —$NR^2$— group, with a compound of the general formula:

X—B—Y  (VIII)

in which B, X and Y have the above-given meanings can here also be a diazo group, whereafter the protective group is again split off, the compound (IV) obtained converted into (V) and this then reacted with a sulphonamide (VI).

When Q is a sulphur atom, it is also possible, instead of the protected compound (VII), to react a compound of the general formula:

HO—A—Q—H  (VIIa)

in which A and Q have the above-given meanings, i.e. a compound (VII) without a protected hydroxyl group, with a compound (VIII), in which case (IV. is obtained directly and then further reacted as described above.

(c) A further process consists in the reaction of a sulphonamide (VI) with a compound of the general formula:

$X^1$—A—$X^2$  (IX)

in which $X^1$ and $X^2$ are two identical or different reactive residues in the meaning in the above-given definition for X, to give a compound of the general formula:

$R^1$—$SO_2$—N—A—$X^2$  (X)
　　　　　|
　　　　　$R^2$ in which A, $R^1$, $R^2$ and $X^2$ have the above-given meanings. By conversion of the $X^2$ group into a —QH group, there is then obtained a compound of the general formula:

$R^1$—$SO_2$—N—A—QH  (XI)
　　　　　|
　　　　　$R^2$ in which A, Q, $R^1$ and $R^2$ have the above-given meanings, which is converted into the desired compound of general formula (I) by reaction with a compound (VIII).

(d) When Q in general formula (I) is an —NH— group, a compound of the general formula:

Z—O—$A^1$—CHO  (XII)

in which $A^1$ is a radical A shortened by one carbon atom and Z has the above-given meaning, is reacted with a compound of the general formula:

$H_2N$—B—Y  (XIII)

in which B and Y have the above-given meanings, or a compound of the general formula:

Z—O—A—NH  (XIV)

in which A and Z have the above-given meanings, is reacted with an aldehyde of the general formula:

OCH—$B^1$—Y  (XV)

in which $B^1$ is a radical B shortened by one carbon atom and Y has the above-given meaning. The Schiff base formed in both cases is hydrogenated to give an amine of the general formula:

Z—O—A—NH—B—Y  (XVI)

in which A, B, Y and Z have the above-given meanings. In the case of $A^1$ and $B^1$, the carbon atom by which these radicals are shortened in comparison with A and B here carries the oxo oxygen.

Since, after splitting off of Z and conversion of the hydroxyl group of compound (XVI) into an X group, this X group can react with the secondary amino group, this amino group must be temporarily protected.

(d1) A process is preferred in which an aldehyde of the general formula:

$R^1$—$SO_2$—N—$A^1$—CHO  (XVII)
　　　　　|
　　　　　$R^2$ in which $A^1$, $R^1$ and $R^2$ have the above-given meanings, is reacted with an amine of general formula (XIII) or in which an amine of the general formula:

$R^1$—$SO_2$—N—A—$NH_2$  (XVIII)
　　　　　|
　　　　　$R^2$ in which A, $R^1$ and $R^2$ have the above-given meanings, is reacted with an aldehyde of general formula (XV) and the Schiff case formed is hydrogenated.

(e) Compounds of general formula (I), in which Q is a sulphinyl group, are prepared by reacting the corresponding sulphenyl compound with an appropriate oxidation agent.

(e1) The preparation of compounds of general formula (I), in which Q is a sulphonyl group, takes place either by oxidation of the corresponding sulphenyl compound or by further oxidation of the corresponding sulphinyl compound with an appropriate oxidation agent.

The reaction of compounds of general formula (III) with compounds of general formula (II) or the reaction of compounds of general formula (VII) with compounds of general formula (VIII) advantageously takes place with the addition of an acid-binding agent. Such an agent can be, for example, an alkali metal carbonate, alkali metal hydroxide or also an alcoholate of a lower aliphatic alcohol. As reaction medium, there can be used, for example, a lower aliphatic alcohol, an aliphatic ketone or an aprotic solvent, such as dimethylformamide or benzene. If it is desired to react a compound (VII) in which Q is an oxygen atom with a compound (VIII), then it is advantageous to use a compound (VIII) in which X is a diazo group. The condensation takes place in the presence of copper powder, for example in ethyl acetate.

The splitting off of the protective group Z takes place by means of processes known from the literature. Thus, for example, a tetrahydropyranyl ether is split by treatment with a warm dilute mineral acid.

The conversion of the free hydroxyl group of compound (IV) into a reactive group X takes place, for example, by reaction with mesyl chloride or tosyl chloride in pyridine, a mesylate or tosylate thereby being formed. However, as reactive group, there can also be used a halogen atom.

For the conversion of aliphatic hydroxyl into halogen, there are available numerous processes. The conversion into bromine is preferred, which takes place either by reaction of the hydroxy compound (IV) with an inorganic acid bromide, for example phosphorus tribromide, or there is first produced a mesylate or tosylate which is then reacted with lithium bromide in acetone, the bromide thereby being obtained in high yield.

The reaction between a compound of general formula (V) and a sulphonamide of general formula (VI) is preferably carried out in such a manner that, in the case of a primary sulphonamide, two moles of sulphonamide are reacted with one mole of sodium alcoholate in an alcohol, the mixture is evaporated and the dry sodium salt is reacted with a compound of general formula (V) in dimethylformamide. However, in the case of a secondary sulphonamide, working is carried out in a mole ratio of 1:1:1. If, for the preparation of compounds of general formula (XVI) or (I) (Q=﹦NH), there is chosen the route via the formation of Schiff bases, then the corresponding aldehyde is advantageously reacted with the necessary primary amine in an appropriate solvent, for example ethanol, and the Schiff base obtained is then reduced, without isolation, by the addition of sodium borohydride. In the case of less active reactants, the formation of the Schiff base is brought about by azeotropic removal of the water formed. The reduction of the Schiff base can also take place by hydrogenation in the presence of r catalyst, for example Raney nickel or palladium-on-charcoal. The oxidation of sulphenyl compounds to sulphinyl or sulphonyl compounds can take place either with an inorganic oxidation agent, for example hydrogen peroxide, sodium periodate, potassium permanganate, sodium ypochlorite or oxone, or with an organic per acid, for example m-chloroperbenzoic acid. As solvent, there can be used water, a lower aliphatic carboxylic acid, for example acetic acid, or a chlorinated hydrocarbon.

The preparation of the sulphinyl compounds takes place by the addition of one equivalent of the oxidation agent in question to the sulphenyl compound.

For the avoidance of the formation of sulphonyl compounds, it is also possible to oxidise with oxygen in the presence of cerium ammonium nitrate in acetonitrile under the conditions described by Riley et al., J. Chem. Soc. Chem. Comm., 1986, 1097.

Also advantageous is the oxidation by means of oxone in methylene chloride in the presence of a phase transfer catalyst analogously to the procedure described by Evans et al., Synth. Comm., 16, 1207/1986.

The preparation of the sulphonyl compounds takes place by the addition of two equivalents of the oxidation agent to the sulphenyl compound or of one equivalent to the sulphinyl compound.

The subsequent introduction of alkyl radicals $R^2$ into a secondary sulphonamide radical takes place by reacting the sodium salt of the sulphonamide with an alkyl halide or an alkyl mesylate or tosylate in a polar solvent, for example dimethylformamide.

The subsequent N-alkylation of a compound of general formula (I), in which Q=—NH—, can be carried out according to known methods. The reaction with an alkyl halide or a dialkyl sulphate in the presence of an acid-binding agent, for example sodium hydroxide, is preferred.

For the acylation of the sulphonamide radical, the secondary sulphonamide ($R^2$=H) is reacted with an acyl halide, a tertiary amine, for example triethylamine or pyridine, thereby being used as hydrogen halide acceptor. As solvent, there is used either an excess of the tertiary amine or an inert solvent, for example methylene chloride, benzene or dimethylformamide. The subsequent introduction of an acyl radical $R^2$ into the secondary amine group (I, Q=—NH—) takes place in the same way. In both cases, instead of the acyl halide, there can also be used a mixed anhydride or an active ester as acylation agent.

The conversion of the substituents Y possibly to be carried out subsequently to the condensation takes place, for example, by saponification of the carboxylic acid esters ($R^4$=alkyl) to the corresponding carboxylic acids ($R^4$=H) with mineral acids or alkali metal hydroxides in a polar solvent, for example water, methanol, ethanol, dioxan or acetone. The saponification is advantageously carried out with a strong base, such as sodium or potassium hydroxide, in a mixture of methanol and water at ambient temperature or at a slightly elevated temperature. On the other hand, the carboxylic acids can also be esterified in the usual way or esters with a particular radical $R^4$ can be converted into esters with a different radical $R^4$ by transesterification. The esterification of the carboxylic acids is advantageously carried out in the presence of an acidic catalyst, for example hydrogen chloride, sulphuric acid or p-toluenesulphonic acid, or in the presence of a strongly acidic ion exchanger resin. Transesterifications, on the other hand, require the addition of a small amount of a basic substance, for example of an alkali metal or alkaline earth metal hydroxide or of an alkali metal alcoholate. For the esterification of the carboxyl group or for the transesterification, in principle there can be used all alcohols. However, it is preferred to use lower monohydroxy alcohols, for example methanol, ethanol or propanol, or alcohols with other functional groups, for example ethanolamine or glycol ether.

The amides according to the present invention derived from the carboxylic acids of general formula (I) are preferably prepared by known methods from the carboxylic acids or reactive derivatives thereof, for example carboxylic acid halides, esters, azides, anhydrides or mixed anhydrides, by reaction with amines. As amine components, there can be used, for example, ammonia, alkylamines and dialkylamines, but also aminoalcohols, for example ethanolamine and 2-aminopropanol, as well as amino acids, for example p-aminobenzoic acid, β-alanine and the like. Other valuable amine components include, for example, alkyl-, aralkyl- and arylpiperazines, as well as 5-aminotetrazole.

For the preparation of compounds of general formula (I) in which Y is —CH$_2$OH, it is preferable to start from compounds (I) in which Y is a carboxyl function (R$^4$=H) or an ester function (R$^4$=alkyl).

For the reduction of the carboxyl function, there can be used all reducing agents conventional for this purpose, for example complex hydrides, such as lithium aluminium hydride or dibal, or borane adducts, for example an adduct of boron trihydride and tetrahydrofuran. However, the reduction can also take place advantageously by reducing a derivative of the carboxylic acid, for example a mixed anhydride of the carboxylic acid and a carbonic acid hemiester. As reducing agent, it is here preferred to use a complex boron hydride, for example sodium borohydride, in a protic solvent.

Numerous processes are known from the literature for the reduction of carboxylic acids to primary alcohols. Here, too, preferred reducing agents are complex aluminium hydrides, for example lithium alanate or DIBAL.

For the preparation of salts with pharmacologically acceptable organic or inorganic bases, for example sodium hydroxide, potassium hydroxide, calcium hydroxide, ammonium hydroxide, methylglucamine, morpholine or ethanolamine, the carboxylic acids can be reacted with the appropriate bases. Mixtures of the carboxylic acids with an appropriate alkali metal carbonate or hydrogen carbonate, can also be considered.

For the production of pharmaceutical compositions, the compounds of general formula (I) are mixed in known manner with appropriate pharmaceutical carrier substances, aroma, flavouring and colouring materials and formed, for example, into tablets or dragees or, with the addition of appropriate adjuvants, suspended or dissolved in water or an oil, for example olive oil.

The compounds of general formula (I) can be administered orally or parenterally in liquid or solid form. As injection medium, it is preferable to use water which contains stabilising agents, solubilising agents and/or buffers usual in the case of injection solutions. Such additives include, for example, tartrate and borate buffers, ethanol, dimethyl sulphoxide, complex formers (such as ethylenediaminetetraacetic acid), high molecular weight polymers (such as liquid polyethylene oxide) for viscosity regulation or polyethylene derivatives of sorbitan anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The dose administered depends upon the age, state of health and weight of the recipient, the extent of the disease, the nature of further treatments possibly carried out simultaneously, the frequency of the treatments and the nature of the desired action. The daily dose of the active compound usually amounts to 0.1 to 50 mg./kg. body weight. Normally, 0.5 to 40 and preferably 1.0 to 20 mg./kg. per day in one or more administrations per day are effective in order to obtain the desired results.

Preferred in the meaning of the present invention are, apart from the compounds of general formula (I) mentioned in the Examples, as well as their esters and amides, also the following:

(1) 8-(4-chlorobenzenesulphonamido)-2,2-dimethyl-4-thiaoctanoic acid
(2) 8-(4-chlorobenzenesulphonamido)-2,2-dimethyl-5-thiaoctanoic acid
(3) 8-(4-chlorobenzenesulphonamido)-2,2-dimethyl-7-thiaoctanoic acid
(4) 8-(4-chlorobenzenesulphonamido)-3,3-dimethyl-4-thiaoctanoic acid
(5) 8-(4-chlorobenzenesulphonamido)-3,3-dimethyl-5-thiaoctanoic acid
(6) 8-(4-chlorobenzenesulphonamido)-3,3-dimethyl-7-thiaoctanoic acid
(7)-8-(4-chlorobenzenesulphonamido)-3-thia-6-eneoctanoic acid
(8)-8-(4-chlorobenzenesulphonamido)-3-thia-6-eneoctanoic acid
(9) 8-(4-chlorobenzenesulphonamido)-3-azaoctanoic acid
(10) N-(4-chlorobenzyl)-8-(4-chlorobenzenesulphonamido)-3-azaoctanoic acid
(11) 8-(4-chlorobenzenesulphonamido)-3-oxaoctanoic acid
(12) 8-(4-fluorobenzenesulphonamido)-2,2-dimethyl-4-thiaoctanoic acid
(13) 8-(4-methylbenzenesulphonamido)-3,3-dimethyl-5-thiaoctanoic acid
(14) 9-(4-chlorobenzenesulphonamido)-2,2-dimethyl-4-thianonanoic acid
(15) 9-(4-chlorobenzenesulphonamido)-2,2-dimethyl-5-thianonanoic acid
(16) 9-(4-chlorobenzenesulphonamido)-2,2-dimethyl-7-thianonanoic acid
(17) 9-(4-chlorobenzenesulphonamido)-2,2-dimethyl-8-thianonanoic acid
(18) 9-(4-chlorobenzenesulphonamido)-3,3-dimethyl-5-thianonanoic acid
(19) 9-(4-chlorobenzenesulphonamido)-3,3-dimethyl-7-thianonanoic acid
(20) 9-(4-chlorobenzenesulphonamido)-3,3-dimethyl-8-thianonanoic acid
(21) (Z)-9-(4-chlorobenzenesulphonamido)-3-thia-6-enenonanoic acid
(22) 9-(4-chlorobenzenesulphonamido)-3-azanonanoic acid
(23) N-methyl-9-(4-chlorobenzenesulphonamido)-3-azanonanoic acid
(24) 9-(3-methylbenzenesulphonamido)-3-thianonanoic acid
(25) 9-(4-fluorobenzenesulphonamido)-3,3-dimethyl-6-thia-nonanoic acid
(26) 8-(4-chlorobenzenesulphonamido)-3,3-dimethyl-6-azaoctanoic acid
(27) 9-(4-chlorobenzenesulphonamido)-3,3-dimethyl-6-azanonanoic acid.

The following Examples are given for the purpose of illustrating the present invention:

EXAMPLE 1

8-(4-Chlorobenzenesulphonamido)-3-thiaoctanoic acid (a) Ethyl 8-(4-chlorobenzenesulphonamido)-3-thioctanoate A solution of 28.4 g. (0.17 mol) 5-bromopentanol and 200 ml. ethanol is added dropwise to a mixture of 20.4 g. (0.17 mol) ethyl thioglycolate, 200 ml. ethanol and 0.17 mol sodium methylate (in the form of a 30% solution). The reaction mixture is heated to reflux temperature for 2 hours and subsequently the ethanol is distilled off in a vacuum. The residue is taken up in diethyl ether, the solution is extracted several times with ice water, then dried over anhydrous sodium sulphate and evaporated. Yield: 31.9 g. (91% of theory) in the form of a colourless oil.

(b) Ethyl 8-(methanesulphonyloxy)-3-thiaoctanoate

A solution of 16.7 g. (0.146 mol) methanesulphonyl chloride and 150 ml. methylene chloride is added dropwise at −5° C., within the course of 30 minutes, to a mixture of 30.1 g. (0.146 mol) ethyl 8-hydroxy-3-thiaoctanoate, 200 ml. methylene chloride and 22,2 g. (0.219 mol) anhydrous triethylamine and the reaction mixture then stirred at 0° C. for a further 30 minutes. It is then extracted with ice-cold 2N sulphuric acid and subsequently with ice water, dried with anhydrous sodium sulphate and subsequently evaporated. Yield 38.3 g. (93% of theory) in the form of a colourless oil.

(c) Ethyl 8-bromo-3-thiaoctanoate.

A mixture of 38.2 g. (0.134 mol) ethyl 8-methanesulphonyloxy)-3-thiaoctanoate, 100 ml. acetone and 23.4 g. (0.269 mol) lithium bromide is stirred for 3 hours at ambient temperature, filtered with suction and the filtrate evaporated. The residue is taken up in methylene chloride, shaken out with water, dried over anhydrous sodium sulphate and evaporated. After chromatography on silica gel with ligroin and diethyl ether (15:1 v/v), there are obtained 24.1 g. (67% of theory) of the desired compound in the form of a colourless oil.

(d) Ethyl 8-(4-chlorobenzenesulphonamido)-3-thiaoctanoate.

A solution of 28.5 g. (0.149 mol) 4-chlorobenzenesulphonamide, 80 ml. methanol and 13.8 ml. of a 30% solution of sodium methylate is briefly stirred and then evaporated to dryness in a vacuum. 20 ml. dimethyl formamide and 20.9 g. (0.0743 mol) ethyl 8-bromo-3-thiaoctanoate are then added thereto and the mixture stirred for 3 hours at 70°-80° C. The reaction mixture is then stirred into ice water and extracted with diethyl ether. The ethereal phase is washed with water, dried with anhydrous sodium sulphate and evaporated. An ethereal solution of the evaporation residue is filtered through a short column of silica gel and then again evaporated. The oily residue crystallises upon triturating with ligroin. After recrystallisation from aqueous ethanol, there are obtained 19.0 g. (67% of theory) of product; m.p. 48°-49° C.

(e) 8-(4-Chlorobenzenesulphonamido)-3-thiaoctanoic acid

A mixture of 5.0 g. (0.013 mol) of the ester obtained according to (d), 20 ml. ethanol and 20 ml. 2 N aqueous sodium hydroxide solution is stirred for 2 hours at 50°-60° C. The ethanol is then distilled off in a vacuum, the residue is mixed with some water and then extracted with diethyl ether. The aqueous phase is then acidified with dilute hydrochloric acid and the precipitated product is filtered off with suction. After recrystallisation from aqueous ethanol, there are obtained 3.6 g. (68% of theory) of the desired product; m.p. 93°-94° C.

EXAMPLE 2

8-(4-Chlorobenzenesulphonamido)-3-thiaoctanoic acid 3-oxide (a) Ethyl 8-(4-chlorobenzenesulphonamido)-3-thiaoctanoate 3-oxide.

A mixture of 5.9 g. (13.2 mmol) ethyl 8-(4-chlorobenzenesulphonamido)-3-thiaoctanoate, 200 ml. ethanol, 150 ml. water and 3.11 g. (14.5 mmol) sodium periodate is stirred for 8 hours at ambient temperature, the ethanol is then distilled off in a vacuum and the evaporation residue is diluted with some water. The aqueous phase is extracted with methylene chloride and the extract is washed with water, then dried over anhydrous sodium sulphate and evaporated. The oily residue is triturated with ligroin and the product which crystallises out is filtered off with suction and recrystallised from ethanol. Yield 4.0 g. (77% of theory); m.p. 85°-86° C.

(b) The free acid is obtained by saponification of the ethyl ester obtained according to (a) in a manner analogous to that described in Example (1e). Yield 76% of theory; m.p. 91°-92° C.

EXAMPLE 3

8-(4-Chlorobenzenesulphonamido)-3-thiaoctanoic acid 3,3-dioxide.

(a) Ethyl 8-(4-chlorobenzenesulphonamido)-3-thiaoctanoate 3,3-dioxide.

A mixture of 5.0 g. (13.2 mmol) ethyl 8-(4-chlorobenzenesulphonamido)-3-thiaoctanoate 3-oxide, 15 ml. ethanol, 8 ml. water and 5.65 g. (26.4 mmol) sodium periodate is kept at reflux temperature for 8 hours and then worked up in the same way as described in Example (2a) Yield 80% of theory; m.p. 55°-57° C., after recrystallisation from ethanol.

(b) The free acid is obtained by saponification of the ester obtained according to (a) in a manner analogous to that described in Example (1e). Yield 73% of theory; m.p. 193°-194° C., after recrystallisation from 66% ethanol.

EXAMPLE 4

9-(4-Chlorobenzenesulphonamido)-3-thianonanoic acid

This is prepared analogously to Example 1 via the following steps:
(a) ethyl 9-hydroxy-3-thianonanoate from 6-chlorohexanol and ethyl thioglycolate; yield 93% cf theory; colourless oil.
(b) ethyl 9-(methanesulphonyloxy)-3-thianonanoate; crude yield 94% of theory; colourless oil.
(c) ethyl 9-bromo-3-thianonanoate; yield 78% of theory; colourless oil.
(d) ethyl 9-(4-chlorobenzenesulphonamido)-3-thianonanoate; yield 72% of theory; colourless oil.
(e) 9-(4-chlorobenzenesulphonamido)-3-thianonanoic acid; yield 51% of theory; m.p. 104°-105° C., after recrystallisation from heptane+ethyl acetate.

EXAMPLE 5

9-(4-Chlorobenzenesulphonamido)-3-thianonanoic acid 3-oxide

This is obtained in a manner analogous to that described in Example 2 by the oxidation of ethyl 9-(4-chlorobenzenesulphonamido)-3-thianonanoate to
(a) ethyl 9-(4-chlorobenzenesulphonamido)-3-thianonanoate; yield 72% of theory; m.p. 72°-74° C.

(after chromatography on silica gel with ethyl acetate) and saponification to (b) the acid; yield 62% of theory; m.p. 105°–106° C., after recrystallisation from approximately 66% ethanol.

EXAMPLE 6

9-(4-Chlorobenzenesulphonamido)-3-thianonanoic acid

This is obtained in a manner analogous to that described in Example 3 by the oxidation of ethyl 9-(4-chlorobenzenesulphonamido)-3-thianonanoate to (a) ethyl 9-(4-chlorobenzenesulphonamido)-3-thianonanoate; yield 92% of theory; colourless oil and saponification to (b) the acid. After chromatography on silica gel with a mixture of 40 volumes methylene chloride, 8 volumes of methanol and 1 volume of water: yield 51% of theory; m.p. 109°–110° C.

EXAMPLE 7

(Z)-9-(4-Chlorobenzenesulphonamido)-3-thia-7-enenonanoic acid (a) Ethyl (Z)-9-tetrahydropyranyloxy-3-thia-7-enenonanoate.

A solution of 70 ml. ethanol and 13.0 g. (59 mmol) (Z)-6-tetrahydropyranyloxy-4-hexenyl chloride is added dropwise at ambient temperature to a mixture of 70 ml. ethanol, 59 mmol sodium methylate (in the form of a 30% methanolic solution) and 7.13 g. (59 mmol) ethyl thioglycolate and the reaction mixture subsequently maintained at reflux temperature for 2 hours.

Thereafter, the ethanol is distilled off in a vacuum and the residue is mixed with ice water and extracted several times with diethyl ether. The ethereal solution is dried with anhydrous sodium sulphate, evaporated and fractionated in a vacuum. Yield 13.4 g. (75% of theory) in the form of a colourless oil; b.p. 165°–167° C./0.13 mbar.

(b) Ethyl (Z)-9-hydroxy-3-thia-7-enenonanoate.

A mixture of 50 ml. ethanol, 15 ml. 2 N sulphuric acid and 11.5 g. (38 mmol) of the tetrahydropyranyloxy compound obtained according to (a) is stirred for 5 hours at 80° C. The ethanol is then distilled off and the residue is poured on to ice and extracted with diethyl ether. The ethereal solution is extracted with a dilute aqueous solution of sodium hydroxide and then with water, dried over anhydrous magnesium sulphate and evaporated. Fractionation in a vacuum gives 3.5 g. (42% of theory) of a colourless oil; b.p. 135° C./0.666 mbar.

(c) Ethyl (Z)-9-methanesulphonyloxy-3-thia-7-enenonanoate.

This is obtained analogously to Example (1b) from the hydroxy compound obtained according to (b) and methanesulphonyl chloride; yield 76% of theory; colourless oil.

(d) Ethyl (Z)-9-bromo-3-thia-7-enenonanoate.

This is obtained analogously to Example (1c) from the methanesulphonyloxy compound obtained according to (c) and lithium bromide; yield 96% of theory; colourless oil.

(e) Ethyl (Z)-9-(4-chlorobenzenesulphonamido)-3-thia-7-enenonanoate.

This is obtained analogously to Example (1d) from the bromo compound obtained according to (d) and 4-chlorobenzenesulphonamide. After chromatography on silica gel with a mixture of diethyl ether (1 volume) and cyclohexane (2 volumes), there is obtained a yield of 62% of theory; colourless oil.

(f) (Z)-9-(4-Chlorobenzenesulphonamido)-3-thia-7-enenonanoic acid.

This is obtained analogously to Example (1e) from the ethyl ester. Yield 81% of theory; colourless oil.

EXAMPLE 8

7-(4-Chlorobenzenesulphonamido)-2,3-dimethyl-5-thiaheptanoic acid (a) Ethyl 7-hydroxy-2,2-dimethyl-5-thiaheptanoate.

A mixture of 5.6 g. (25.1 mmol) ethyl 4-bromo-2,2-dimethylbutanoate, 50 ml. ethanol, 25.1 mmole sodium methylate (in the form of a 30% methanolic solution) and 2.0 g. 2-mercaptoethanol is stirred for 3 hours at ambient temperature and thereafter evaporated in a vacuum. Water is now added thereto and extracted with diethyl ether. The ethereal solution is extracted with cold 1N aqueous sodium hydroxide solution, dried with anhydrous sodium sulphate and evaporated.

(b) Ethyl 7-bromo-2,2-dimethyl-5-thiaheptanoate.

By the reaction of the hydroxy compound obtained according to (a) with methanesulphonyl chloride analogously to Example (1b), there is obtained the corresponding methanesulphonyloxy compound which is reacted analogously to Example (1c) with lithium bromide to give the corresponding bromo compound. The crude yield is almost quantitative; colourless oil.

(c) Ethyl 7-(4-chlorobenzenesulphonamido)-2,2-dimethyl-5-thiaheptanoate.

This is obtained analogously to Example (1d) from the bromo compound obtained according to (b) and 4-chlorobenzenesulphonamide; yield 68% of theory; colourless oil.

(d) 7-(4-Chlorobenzenesulphonamido)-2,2-dimethyl-5-thiaheptanoic acid.

This is obtained by saponification of the ethyl ester analogously to Example (1e). Yield 84% of theory; m.p. 112°–113° C.

In analogy thereto, there can be prepared: 2. 8-(4-Chlorobenzenesulphonamido)-2,2-dimethyl-6-thiaoctanoic acid via the following steps:

(a) Ethyl 8-hydroxy-2,2-dimethyl-6-thiaoctanoate from ethyl 5-bromo-2,2-dimethyl-pentanoate and 2-mercaptoethanol. Crude yield almost quantitative; colourless oil;

(b) Ethyl 8-bromo-2,2-dimethyl-6-thiaoctanoate from ethyl 8-hydroxy-2,2-dimethyl-6-thiaoctanoate and methanesulphonyl chloride and subsequent reaction of the resultant methanesulphonyloxy compound with lithium bromide. Yield 62% of theory; colourless oil;

(c) Ethyl 8-(4-chlorobenzenesulphonamido)-2,2-dimethyl-6-thiaoctanoate from ethyl 8-bromo-2,2-dimethyl-6-thiaoctanoate and 4-chlorobenzenesulphonamide; yield 63% of theory; colourless oil;

(d) 8-(4-Chlorobenzenesulphonamido)-2,2-dimethyl-6-thiaoctanoic acid by saponification of the ethyl ester; yield 96% of theory; m.p. 107°–109° C. 3. 8-(4-Chlorobenzenesulphonamido)-3,3-dimethyl-6-thiaoctanoic acid via the following steps:

(a) Ethyl 8-hydroxy-3,3-dimethyl-6-thiaoctanoate

A mixture of 50 ml. dimethyl sulphoxide and 42.2 mmol sodium hydride is maintained at 80° C. for 45 minutes. It is then cooled to ambient temperature, 3.3 g.

(42,2 mmol) 2-mercaptoethanol and then 10.0 g. (42,2 mmol) ethyl 5-bromo-3,3-dimethylpentanoate are added thereto and the reaction mixture is stirred for 3 hours at ambient temperature. It is then poured into water and extracted with diethyl ether. The ethereal phase is dried with anhydrous sodium sulphate and then evaporated. After chromatography of the residue on silica gel with a mixture of equal parts by volume of diethyl ether and cyclohexane, there are obtained 6.8 g. (70% of theory) of the desired product in the form of a colourless oil.

(b) Ethyl 8-bromo-3,3-dimethyl-6-thiaoctanoate

This is obtained from ethyl 8-hydroxy-3,3-dimethyl-6-thiaoctanoate and methanesulphonyl chloride and subsequent reaction of the resultant methanesulphonyloxy compound with lithium bromide. Crude yield quantitative; colourless oil.

(c) Ethyl 8-(4-chlorobenzenesulphonamido)-3,3-dimethyl-6-thiaoctanoate

This is obtained from ethyl 8-bromo-3,3-dimethyl-6-thiaoctanoate and 4-chlorobenzenesulphonamide. After chromatography on silica gel with a mixture of 2 parts by volume of diethyl ether and 7 parts by volume of ligroin, there is obtained a yield of 71% of theory of the desired product; colourless oil.

(d) 8-(4-Chlorobenzenesulphonamido)-3,3-dimethyl-6-thiaoctanoic acid

This is obtained by saponification of the ethyl ester; yield 92% of theory; colourless oil. 4. 9-(4-Chlorobenzenesulphonamido)-2,2-dimethyl-3-thianonanoic acid via the following steps:

(a) Ethyl 9-hydroxy-2,2-.dimethyl-3-thianonanoate

This is obtained analogously to Example (8a) from ethyl 2-bromo-2-methylpropionate and 6-mercaptohexanol; crude yield 74% of theory; colourless oil; $n_D^{20} = 1.4890$.

(b) Ethyl 9-bromo-2,2-dimethyl-3-thianonanoate

This is obtained from ethyl 9-hydroxy-2,2-dimethyl-3-thianonanoate and methanesulphonyl chloride and subsequent reaction of the resultant methanesulphonyloxy compound with lithium bromide. Yield after chromatography on silica gel/cyclohexane 57% of theory; colourless oil; $n_D^{20} = 1.4916$.

(c) Ethyl 9-(4-chlorobenzenesulphonamido)-2,2-dimethyl-3-thianonanoate

This is obtained from ethyl 9-bromo-2,2-dimethyl-3-thianonanoate and 4-chlorobenzenesulphonamide. After chromatography on silica gel/cyclohexane+diethyl ether (1:1 v/v) yield 81% of theory; colourless oil; $n_D^{20} = 1.5175$.

(d) 9-(4-Chlorobenzenesulphonamido)-2,2-dimethyl-3thianonanoic acid

This is obtained by saponification of the ethyl ester. After chromatography on silica gel/methylene chloride yield 67% of theory; m.p. 93°-94° C.

EXAMPLE 9

8-(4-Chlorobenzenesulphonamido)-2,2-dimethyl-3-thiaoctanoic acid (a) Ethyl 8-hydroxy-2,2-dimethyl-3-thiaoctanoate.

This is prepared analogously to Example (8a) from 5-mercaptopentanol and ethyl 2-bromo-2-methylpropionate; crude yield 75% of theory; colourless oil; $n_D^{20} = 1.4800$ (contains some methyl ester).

(b) Ethyl 8-bromo-2,2-dimethyl-3-thiaoctanoate.

This is prepared from ethyl 8-hydroxy-2,2-dimethyl-3-thiaoctanoate and methanesulphonyl chloride and subsequent reaction of the resultant methanesulphonyloxy compound with lithium bromide. Yield 86% of theory; colourless oil; $n_D^{20} = 1.4936$ (contains some methyl ester).

(c) Ethyl 8-(4-chlorobenzenesulphonamido)-2,2-dimethyl-3-thiaoctanoate.

This is prepared from ethyl 8-bromo-2,2-dimethyl-3-thiaoctanoate and 4-chlorobenzenesulphonamide. After chromatography on silica gel/cyclohexane+diethyl ether (1:1 v/v), the yield is 79% of theory; colourless oil; $n_D^{20} = 1.5331$ (contains some methyl ester).

(d) 8-(4-Chlorobenzenesulphonamido)-2,2-dimethyl-3-thiaoctanoic acid.

This is obtained by saponification of the ethyl ester. After chromatography on silica gel/methylene chloride, the yield is 64% of theory; m.p. 98° C., after recrystallisation from toluene.

In an analogous way, there are obtained: 2. 8-(4-Methoxybenzenesulphonamido)-2,2-dimethyl-3-thiaoctanoic acid by reaction of ethyl 8-bromo-2,2-dimethyl-3-thiaoctanoate with 4-methoxybenzenesulphonamide to give (a) ethyl 8-(4-methoxybenzenesulphonamido)-2,2-dimethyl-3-thiaoctanoate; after chromatography on silica gel/cyclohexane+diethyl ether (2:1 v/v), the yield is 69% of theory; colourless oil; $n_D^{20} = 1.5280$ and subsequent saponification of this ester to give (b) the desired acid; yield 90% of theory; m.p. 57°-59° C. 3. 8-(3-Trifluoromethylbenzenesulphonamido)-2,2-dimethyl-3-thiaoctanoic acid by reaction of ethyl 8-bromo-2,2-dimethyl-3-thiaoctanoate with 3-trifluoromethylbenzenesulphonamide to give (a) ethyl 8-(3-trifluoromethylbenzenesulphonamido)-2,2-dimethyl-3-thiaoctanoate; after chromatography on silica gel/cyclohexane+diethyl ether (2:1 v/v), the yield is 75% of theory; colourless oil; $n_D^{20} = 1.4930$ and subsequent saponification of this ester to give (b) the desired acid; yield 88% of theory; m.p.93°-94° C.

EXAMPLE 10

9-(4-Chlorobenzenesulphonamido)-3,3-dimethyl-4-thianonanoic acid (a) Ethyl 9-methanesulphonyloxy-3,3-dimethyl-4-thianonanoate.

To a mixture of 4.0 g. (16.1 mmol) ethyl 9-hydroxy-3,3-dimethyl-4-thianonanoate (prepared from ethyl β,β-dimethylacrylate and 5-mercaptoethanol analogously to the method of Vovrek et al., J. med. Chem., 15, 125/1972), 3.26 g. (32,2 mmol) anhydrous triethylamine and 25 ml. methylene chloride is added dropwise at 0° C. a solution of 1.85 g. (16.1 mmol) methanesulphonyl chloride and 20 ml. methylene chloride. The reaction mixture is stirred for 1 hour at ambient temperature and subsequently washed with ice-cold 1 N hydrochloric acid and ice water. It is then dried with anhydrous magnesium sulphate and evaporated in a vacuum. Yield 5.1 g. (96% of theory); colourless oil.

(b) Ethyl 9-bromo-3,3-dimethyl-4-thianonanoate.

A mixture of 5.0 g. (15.3 mmol) ethyl 9-methanesulphonyloxy-3,3-dimethyl-4-thianonanoate, 25 ml. acetone and 1.5 g. (17.3 mmol) lithium bromide is stirred for 8 hours at ambient temperature and then evaporated in a vacuum. Diethyl ether and water are added to the residue, shaken up and the ethereal phase is separated off. The aqueous phase is again extracted with diethyl ether. The combined ethereal phases are dried with anhydrous sodium sulphate and evaporated. The residue is purified by chromatographing on a silica gel column with cyclohexane+diethyl ether (2:1 v/v). Yield 3.6 g. (76% of theory); colourless oil.

(c) Ethyl 9-(4-chlorobenzenesulphonamido)-3,3-dimethyl-4-thianonanoate.

This is obtained after reacting the bromo ester obtained according to (b) with 4-chlorobenzenesulphonamide analogously to Example (1d). After chromatography on a silica gel column with cyclohexane+diethyl ether (2:1 v/v), there is obtained a yield of 57% of theory; colourless oil; $n_D^{20} = 1.5290$.

(d) 9-(4-Chlorobenzenesulphonamido)-3,3-dimethyl-4-thianonanoic acid.

This is obtained by saponification of the ethyl ester obtained according to (c) in a manner analogous to that described in Example (1e). Yield 71% of theory; m.p. 46°–48° C.

EXAMPLE 11

9-(4-Chlorobenzenesulphonamido)-2,2-dimethyl-6-thianonanoic acid (a) Ethyl 9-(4-chlorobenzenesulphonamido)-2,2-dimethyl-6-thianonanoate.

This is obtained by reacting 3-(4-chlorobenzenesulphonamido)-propylmercaptan with ethyl 5-bromo-2,2-dimethylpentanoate analogously to Example (8a). After chromatography on silica gel/cyclohexane+ethanol (100+1.2 vol.), there is obtained a yield of 61% of theory; colourless oil.

(b) The desired acid is obtained by saponifying the ethyl ester analogously to Example (1e). Yield 91% of theory; colourless oil.

The following compound is prepared in an analogous way:

2. 9-(4-Chlorobenzenesulphonamido)-3,3-dimethyl-6-thianonanoic acid.

(a) Ethyl 9-(4-chlorobenzenesulphonamido)-3,3-dimethyl-6-thianonanoate.

This is obtained by reacting 3-(4-chlorobenzenesulphonamido)-propylmercaptan with ethyl 5-bromo-3,3-dimethyl-pentanoate analogously to Example (8a). After chromatography on silica gel/cyclohexane+diethyl ether (8:2 v/v), there is obtained a yield of 66% of theory; colourless oil.

(b) The desired acid is obtained by saponifying the ethyl ester analogously to Example (1e). After chromatography on silica gel/cyclohexane+ethanol (8:2 v/v), there is obtained a yield of 71% of theory; colourless oil.

EXAMPLE 12

9-(4-Chlorobenzenesulphonamido)-3-oxanonanoic acid (a) To a suspension of 0.4 g. of copper powder in a gently boiling solution of 5.0 g. 6-bromohexanol in 15 ml. ethyl acetate is added dropwise, with vigorous stirring, over a period of 15 minutes, a cold solution of 2.5 g. ethyl diazoacetate in 5 ml. ethyl acetate. Thereafter, the reaction mixture is stirred under reflux for 4 hours. After cooling, the solution is filtered and the solvent is distilled off in a vacuum, 4.7 g. of an oily residue thereby being obtained. To the residue are added 35 ml. ethyl acetate, 5.0 g. 6-bromohexanol and, in addition, 0.4 g. copper powder and the above-described reaction is repeated, a solution of 3.4 g. ethyl diazoacetate in 15 ml. ethyl acetate thereby being added thereto. After distilling off the solvent, 9.2 g. of an amber-coloured oil are obtained which is purified over a silica gel column with chloroform. There are obtained 5.2 g. ethyl 6-bromohexyloxyacetate in the form of a colourless oil.

(b) A mixture of 2.0 g. ethyl 6-bromohexyloxyacetate, 4.0 g. 4-chlorobenzenesulphonamide and 8.7 g. anhydrous potassium carbonate in 25 ml. dry dimethylformamide is stirred for 4 hours at 110°–120° C. The mixture is evaporated in a vacuum until a greasy slurry is obtained to which water and dichloromethane are added. The organic phase is washed with water, dried and evaporated, 4.4 g. of an orange-coloured oil being obtained. Purification takes place with a chloroform/ethyl acetate mixture on a silica gel column. There are obtained 800 mg. ethyl 9-(4-chlorobenzenesulphonamido)-3-oxanonanoate in the form of a colourless oil.

(c) 700 mg. Ethyl 9-(4-chlorobenzenesulphonamido)-3-oxanonanoate are hydrolysed with a warm mixture of dilute aqueous sodium hydroxide solution and ethanol. The mixture is evaporated in a vacuum to 20% of its volume, extracted with diethyl ether and acidified with dilute sulphuric acid to about pH 2. The mixture is extracted with dichloromethane and the dried extract is evaporated, a colourless oil being obtained which becomes solid after standing for a comparatively long period of time. After recrystallisation from dichloromethane/diethyl ether, there are obtained 300 mg. 9(9-(4-chlorobenzenesulphonamido)-3-oxanonanoic acid; m.p 91°–92° C.

It will be understood that the specification and examples are illustrative but not limitative of the present invention and that other embodiments within the spirit and scope of the invention will suggest themselves to those skilled in the art.

PROTOCOL OF EXPERIMENT

1. TX Antagonistic Effect of Human Erythrocyn

Method

The thrombocyte aggregation is investigated by the method of Born and Cross (J. Physiol. 168, 178 (1963) in platelet-rich plasma of healthy blood donors. To inhibit clotting, the blood is mixed with 3.2% citrate in a ratio by volume of 1:9.

To induce thrombocyte aggregation, U 46619 (Upjohn & Co., Kalamazoo, USA), which is a stable analog of the prostaglandin endoperoxide $PHG_2$, is used. U 46619 was characterized as a selective thromboxane mimetic (Coleman et al., Brit. J. Pharmacol. 68, 127 P., 1980).

The aggregation test is carried out in a 4-channel aggregometer (Profiler ® of the Bio/Data Co., USA). The course of the aggregation is followed over a period of 5 minutes. At the end of the test, the degree of aggregation attained is printed out. These values, which are obtained in the presence of different concentrations of the substance to be tested, are used for the determination of the $IC_{50}$ for the TX antagonistic effect. The effectiveness varies inversely with the $IC_{50}$ value.

2. Preventing the U 46619-Induced Pulmonary Embolism

Method

Male NMRI mice, with a body weight of 25 g. are used. The test substance is suspended in 1% methylcellulose and administered to the experimental animals with the help of a stomach tube. The provocation test consists of injecting the lethal dose (800–1000/µg/kg)

of the thromboxane mimetic (U 46619 of the Upjohn Co.) rapidly into the tail vein. The duration of the specific antagonistic effect is tested by pretreating the animals with 25 mg or 1 mg/kg of the different test substances and injecting U 46619 after 4 hours. The survival rate indicates how many of the animals used have survived the injection of the thromboxane mimetic. The results are given in the Table below:

| Substance Example | Survival Rate of Mouse 25 mg/kg, 4 h in % | Survival Rate of Mouse 1 mg/kg, 4 h in % | Thromboxane Aggregation IC50 ($\mu$M) |
|---|---|---|---|
| 8.3 | 40 | | 5.0 |
| 4 | 40 | | 1.3 |
| 5 | 40 | | 2.1 |
| 7 | 100 | 60 | 1.4 |
| 6 | 80 | 100 | 3.4 |
| 8 | 40 | | 13.0 |
| 9 | 40 | | 5.2 |
| 9.2 | 60 | 20 | 100.0 |
| 11 | 80 | 0 | 60.0 |
| 11.2 | 80 | 0 | 100.0 |

We claim:
1. A compound of the formula:

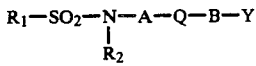

wherein
R$_1$ is a C$_1$–C$_6$ alkyl, C$_2$–C$_6$ alkenyl, C$_3$–C$_7$ cycloalkyl or an aralkyl, aralkenyl or aryl radical in which the aryl can be substituted one or more times by halogen C$_1$–C$_6$-alkyl, C$_1$–C$_6$-alkoxy, hydroxyl, trifluoromethyl, cyano, nitro, amino, C$_1$–C$_6$-acylamino, C$_2$–C$_{12}$-dialkylamino, C$_1$–C$_6$-alkylamino C$_1$–C$_{16}$-acyl, C$_1$–C$_6$-alkylsulphenyl, -sulphinyl or -sulphonyl or by azido,
R$_2$ is hydrogen or C$_1$–C$_6$-alkyl, aralkyl, aralkenyl or acyl
A and B are saturated or unsaturated C$_1$–C$_{10}$ alkylene chains which can be unsubstituted or substituted once or twice by a C$_1$–C$_3$-alkyl which together can also form an alkylene chain —(CH$_2$)$_m$— in which m is 2, 3, 4 or 5 the sum of carbon atoms in chains A and B being at least 4 and at most 11,
Q is oxygen, sulphur, sulphonyl or sulphinyl or an amino group —N—(R$_2$)— wherein, R$_2$ has the same meaning as above,
Y is a free carboxylic acid group or a carboxylic acid ester, carboxylic acid amide, hydroxymethyl or tetrazolyl; and the pharmacologically acceptable salts thereof, the optically-active isomers and E-Z isomers thereof when A and B are alkene, and mixtures thereof.
2. The compound of claim 1, wherein A is —(CH$_2$)$_n$—, wherein n is a whole number from 1 to 6, or A is —(CH$_2$)$_m$—CH=CH—(CH$_2$)$_n$—, wherein m is 1 or 2 and n is 2, 3, 4 or 5.
3. The compound of claim 1, wherein B is —(CH$_2$)$_p$—, wherein p is a whole number from 1 to 7, or B is —(CH$_2$)$_q$—C(CH$_3$)$_2$— wherein q is 0 or a whole number from 1 to 6, or B is —(CH$_2$)$_r$—C(CH$_3$)$_2$—CH$_2$—, wherein r is 0 or a whole number from 1 to 5.
4. The compound of claim 1 wherein the substituent in the A and B chain is methyl or ethyl.

5. The compound of claim 1 wherein if the two substituents of the A and B chain together are —(CH$_2$)$_m$— then m is 5 and forms the basis of a six-membered ring when the substituents are on the same carbon.
6. The compound of claim 1 wherein R$_1$ is methyl, ethyl, propyl, propenyl, cyclopentyl, cyclohexyl, cycloheptyl, benzyl, phenethyl, cinnamyl, phenyl or naphthyl and the phenyl can be substituted one or more times by halogen, methyl, methoxy, trifluoromethyl, cyano, nitro, amino, hydroxyl, methylamino, diethylamino, acetamino, acetyl, octanoyl, hexadecanoyl, methylsulphenyl, methylsulphinyl, methylsulphonyl or azide.
7. The compound of claim 1 wherein R$_1$ is 4-chlorophenyl, 4-bromophenyl, 4-fluorophenyl, 3-trifluorophenyl, 4-methylphenyl, 4-cyanophenyl, 4-methoxyphenyl or 3-methylphenyl.
8. The compound of claim 1, wherein R$_1$ is a 4-chlorophenyl, 4-methoxyphenyl or 4-trifluoromethylphenyl.
9. The compound of claim 1 wherein R$_2$ is hydrogen, methyl, benzyl, 4-chlorobenzyl, cimmanoyl, 4-chlorocinnamyl, benzoyl or acetyl.
10. The compound of claim 1 wherein the halogen is fluorine, chlorine or bromine.
11. A substituted sulphonamide compound selected from the group consisting of
9-(4-Chlorobenzenesulphonamido)-3-thianonanoic acid,
9-(4-Chlorobenzenesulphonamide)-3-thianonanoic acid 3-oxide,
9-(4-Chlorobenzenesulphonamido)-3-thianonanoic acid; (Z)-9-(4-Chlorobenzenesulphonamido)-3-thia-7-ene-nonanoic acid,
7-(4-Chlorobenzenesulphonamido)-2,3-dimethyl-5-thiaheptanoic acid,
8-(4-Chlorobenzenesulphonamido)-3,3-dimethyl-6-thiaoctanoic acid,
8-(4-Chlorobenzenesulphonamido)-2,2-dimethyl-3-thiaoctanoic acid,
8-(4-Methoxybenzenesulphonamido)-2,2-dimethyl-3-thiaoctanoic acid,
9-(4-Chlorobenzenesulphonamido)-2,2-dimethyl-6-thianonanoic acid, and
9-(4-Chlorobenzenesulphonamido)-3,3-dimethyl-6-thianonanoic acid.
12. A pharmaceutical composition to inhibit thrombocyte aggregation or treat pulmonary embolism comprising a pharmaceutically effective amount of the compound of claim 1 in a pharmaceutically acceptable carrier.
13. A pharmaceutical composition to inhibit thrombocyte aggregation or treat pulmonary embolism comprising a pharmaceutically effective amount of at least one compound of claim 11 in a pharmaceutically acceptable carrier.
14. A method for the inhibition of thrombocyte aggregation or treatment or prevention of pulmonary embolism comprising
administering to a patient in need of said treatment a pharmaceutically effective amount of the compound of claim 1 in a pharmaceutically acceptable carrier.
15. A method for the inhibition of thrombocyte aggregation or prevention or treatment of pulmonary embolism comprising administering to a patient in need of said treatment a pharmaceutically effective amount of the compound of claim 11 in a pharmaceutically acceptable carrier.

16. The method of claim 14 comprising administering to said patient a daily dose of the active compound of 0.1 to 50 mg/kg body weight.

17. The method of claim 15 comprising administering to said patient a daily dose of the active compound of 0.1 to 50 mg/kg body weight.

18. The method of claim 14 comprising administering to said patient a daily dose of 1.0 to 20 mg/kg body weight.

19. The method of claim 15 comprising administering to said patient a daily dose of 1.0 to 20 mg/kg body weight.

* * * * *

UNITED STATES PATENT AND TRADEMARK OFFICE
CERTIFICATE OF CORRECTION

PATENT NO. : 4,981,873
DATED : January 1, 1991
INVENTOR(S) : Ernst-Christian Witte, et al.

It is certified that error appears in the above-identified patent and that said Letters Patent is hereby corrected as shown below:

| | |
|---|---|
| Col. 3, line 39: | change "(IV." to --(IV)--. |
| Col. 4, line 15: | change "Z-O-A-NH" to -- Z-O-A-$NH_2$ --. |
| Col. 5, line 51: | after "of" change "r" to -- a --. |
| Col. 8, line 19: | before "-8-" insert -- (Z) -- to have formula read "(Z)-8-(4-". |
| Col. 8, line 21: | before "-8-" insert -- (E) -- to have formula read "(E)-8-(4-chlorobenzenesulphonamido)-3-thia-6-eneoctanoic acid". |
| Col. 16, line 26: | change "9(9-(4-" to -- 9-(4- --. |

Signed and Sealed this

Fifth Day of January, 1993

Attest:

DOUGLAS B. COMER

*Attesting Officer*    *Acting Commissioner of Patents and Trademarks*